(12) United States Patent
Josel et al.

(10) Patent No.: US 8,460,944 B2
(45) Date of Patent: Jun. 11, 2013

(54) USE OF A BIS-MALEIC ANHYDRIDE CROSS-LINKING AGENT FOR FIXATION OF A CELL OR TISSUE SAMPLE

(75) Inventors: Hans-Peter Josel, Weilheim (DE); Michael Gerg, Munich (DE); Rupert Herrmann, Weilheim (DE); Rosa Isabel Saez Diaz, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/400,862

(22) Filed: Feb. 21, 2012

(65) Prior Publication Data

US 2012/0149019 A1 Jun. 14, 2012

Related U.S. Application Data

(63) Continuation of application No. PCT/EP2010/005085, filed on Aug. 19, 2010.

(30) Foreign Application Priority Data

Aug. 21, 2009 (EP) .................................. 09010767

(51) Int. Cl.
| | |
|---|---|
| G01N 33/557 | (2006.01) |
| G01N 33/543 | (2006.01) |
| G01N 33/556 | (2006.01) |
| C12Q 1/68 | (2006.01) |
| C07D 407/00 | (2006.01) |
| B01L 3/00 | (2006.01) |

(52) U.S. Cl.
USPC ........... 436/517; 436/518; 436/521; 549/231; 549/233; 549/252; 435/6.1; 422/430

(58) Field of Classification Search
USPC ............ 549/231, 252, 233; 435/6.1; 436/521, 436/517, 518; 422/430
See application file for complete search history.

(56) References Cited

U.S. PATENT DOCUMENTS

| | | |
|---|---|---|
| 2002/0182653 A1 | 12/2002 | Namimatsu |
| 2005/0255540 A1 | 11/2005 | Fredenburgh et al. |

OTHER PUBLICATIONS

International Search Report issued Nov. 5, 2010 in PCT Application No. PCT/EP2010/005085, 5 pages.
Bowers, Simeon et al., "N-Bridged bicyclic sulfonamides as inhibitors of _-secretase," Bioorganic & Medicinal Chemistry Letters, 2009, pp. 6952-6956, vol. 19.
Database Biosis [Online], Lodin, Z. et al., "Correlation between changed Biophysical Properties of Surface Membranes and Embryonic Brain Cell Adhesivity Influence of Detergents Fixation EGTA Colchicine Vinblastine Increased Potassium Ouabain and DMA on the Primary Cellular Adhesivity of Embryonic Brain Cell," Biosciences Information Service, 1987, Database Accession No. PREV198784017625, Abstract.

*Primary Examiner* — Jezia Riley
(74) *Attorney, Agent, or Firm* — Faegre Baker Daniels LLP (57) ABSTRACT

The present disclosure relates to novel bis-maleic anhydrides and to the surprising discovery that bis-maleic anhydride cross-linking agents can be used for preservation/fixation of a cell or tissue sample. Various bis-maleic anhydride cross-linking agent scan be used in methods requiring fixation of a cell or tissue sample. These reagents and methods are especially useful in procedures that require that the fixation agent be removed in order to facilitate analysis with other reagents. The inventive reagents and methods make it easier to reliably assay for various proteins, a nucleic acid and the like using analytical methods such as like immunohistochemistry, fluorescence in situ hybridization, RT-PCR, and the like.

14 Claims, 4 Drawing Sheets

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Forward Primer for HER2

<400> SEQUENCE: 1
ctcagcgtac ccttgtcc                                                    18

<210> SEQ ID NO 2
<211> LENGTH: 19
<212> TYPE: DNA
<213> ORGANISM: Artificial Sequence
<220> FEATURE:
<223> OTHER INFORMATION: Reverse Primer for HER2

<400> SEQUENCE: 2
tgtcaggcag atgcccaga                                                   19

<210> SEQ ID NO 3
<211> LENGTH: 26
<212> TYPE: DNA
<213> ORGANISM: Artificial Sequence
<220> FEATURE:
<223> OTHER INFORMATION: Probe for HER2

<400> SEQUENCE: 3
tggtgtgggc tccccatatg tctccc                                           26

<210> SEQ ID NO 4
<211> LENGTH: 22
<212> TYPE: DNA
<213> ORGANISM: Artificial Sequence
<220> FEATURE:
<223> OTHER INFORMATION: Forward Primer for EGFR

<400> SEQUENCE: 4
tgaaaacacc gcagcatgtc aa                                               22

```
<210> SEQ ID NO 5
<211> LENGTH: 26
<212> TYPE: DNA
<213> ORGANISM: Artificial Sequence
<220> FEATURE:
<223> OTHER INFORMATION: Reverse Primer for EGFR

<400> SEQUENCE: 5
ctccttctgc atggtattct ttctct                                          26

<210> SEQ ID NO 6
<211> LENGTH: 25
<212> TYPE: DNA
<213> ORGANISM: Artificial Sequence
<220> FEATURE:
<223> OTHER INFORMATION: Probe for EGFR

<400> SEQUENCE: 6
tttgggctgg ccaaactgct gggtg                                           25
```

USE OF A BIS-MALEIC ANHYDRIDE CROSS-LINKING AGENT FOR FIXATION OF A CELL OR TISSUE SAMPLE

PRIORITY CLAIM

This application is a continuation of International Application No. PCT/EP2010/005089, filed Aug. 19, 2010, which claims the benefit of European Patent Application No. 09010767.3, filed Aug. 21, 2009, the disclosures of which are hereby incorporated by reference in their entirety.

SEQUENCE LISTING

The instant application includes a Sequence Listing which has been submitted in ASCII format via EFS-Web and is hereby incorporated by reference in its entirety. Said ASCII copy, created on Feb. 3, 2012, is named Sequence_Listing_26291_US.txt, and is 1,413 bytes in size.

FIELD OF THE DISCLOSURE

The present disclosure relates to novel bis-maleic anhydrides. It especially relates to the discovery that bis-maleic anhydride cross-linking agents can be used for preservation/fixation of a cell or tissue sample. With great advantage a bis-maleic anhydride cross-linking agent can be used in methods requiring fixation of a cell or tissue sample and at the same time requiring that the fixative has little impact on the later detection of a protein or a nucleic acid in procedures like immunohistochemistry, fluorescence in situ hybridization or RT-PCR. It is also demonstrated that the use of a bis-maleic anhydride cross-linking agent as a fixative greatly facilitates later detection of an analyte of interest in a previously fixed cell or tissue sample.

BACKGROUND

To date there is no generally applicable, "ideal" way to prepare a cell or tissue sample, e.g. for immunohistochemistry or detection of a nucleic acid of interest, respectively. Fixation and the reversibility of negative effects introduced by the fixation process have a major impact on the detectability of polypeptide antigens and nucleic acids, respectively, and on the reproducibility of the results obtained thereupon.

For successful immunostaining of an antigen in a cell or tissue sample at least three criteria have to be met: a) retention of the antigen at its original site, b) accessibility of the antigen and c) correct conformation/preservation of the antigen/epitope of interest. It appears that at present no fixation and/or detection procedure fully meets all these three criteria. For most procedures known in the art, best performance for one or two of these criteria often occurs at the expense of reduced performance in at least one other criterion.

Several fixatives are available and are routinely used by clinical pathology laboratories. These fixatives include glutardialdehyde, formaldehyde, and acetone, or other organic solvents. The vast majority of fixation procedures are based on the use of cross-linking agents, like formaldehyde. The fixative solution usually is an aqueous formaldehyde solution that includes sodium phosphates, formulated to provide buffering (minimal pH change following addition of a small amount of strong acid or base) to pH 7.2-7.6 and an approximately isotonic solution (a solution with the same or nearly the same osmotic pressure as that of mammalian extracellular fluids, isotonic solutions are based on physiological saline).

In order to perform many state-of-the-art procedures sample fixation has to be virtually perfect.

If fixation is incomplete, instead of fixation one merely observes the coagulation of proteins caused by the reagents and/or conditions used to dehydrate the sample. This may, for example, negatively impact the preservation of the sample tissues, or their morphology or impair their long term stability.

A prolonged formaldehyde fixation step may resort in the formation of cross-linked protein molecules that form a dense network. This network can impair the penetration of paraffin wax into the sample or/and the access of antibody molecules to epitomes of interest in the sample. As a result an antigen of interest may be reversibly or even irreversibly masked. Further an epitope may be chemically modified ("destroyed") e.g., by reaction with formaldehyde.

In addition, it is known that the activity of most enzymes is impaired after formaldehyde fixation.

Fixation in formaldehyde is among the most widely used procedure in clinical pathology. The most likely primary reason that this reagent is used is that fixation with formaldehyde may trap an antigen of interest at the site that it occupies in the living organism. The methylene bridges introduced upon formaldehyde fixation also help to preserve the morphology of the cell or tissue in a given sample. These positive effects, however, occur at the expense of permeability, and fixation of the sample may, for example, cause: changes in the accessibility and/or conformation of an antigen/epitope of interest; damage to nucleic acids; and inactivation of enzymes of interest in the fixed sample.

Cross-linking due to formaldehyde fixation may mask or destroy epitopes, leading to a false negative immuno-staining result. This failure is more likely to occur when the primary immuno-reagent is a monoclonal antibody than when the primary immuno-reagent is a polyclonal antiserum. These problems with formaldehyde fixation have lead to many attempts to reduce or eliminate the negative effects of formaldehyde fixation; many of these attempts are chronicled in the scientific literature.

For long term storage a fixed cell or tissue sample usually has to be de-hydrated and embedded in an appropriate embedding medium. Paraffin embedding is usually preferable to either plastic embedding or cutting un-embedded specimens with a vibrating microtome or in a cryostat.

As illustrated above, all fixation procedures to a certain extent represent compromises of various kinds. Often optimal preservation of morphology goes to the expense of accessibility for an antibody or destruction of an antigen or of an epitope thereon.

However, and important to the present disclosure, not only is there a high variability introduced during preparation of a specimen, like its fixation or further processing like embedding with paraffin, probably even more variability is caused by the various modes and routes of regaining immunological reactivity or accessibility in detection of nucleic acids, i.e. in procedures known as antigen retrieval.

Despite the broad use and great utility of e.g. immunohistochemical methods or methods for detecting a nucleic acid of interest in a cell or tissue sample there is a great need for further improvements. Such improvements may, for example, relate to more gentle fixation of a cell or tissue sample, to improvements in antigen retrieval or/and to better comparability and reproducibility of results and maybe even include the possibility of using antibodies for which the corresponding antigen or epitope is destroyed in standard procedures, like fixation with formaldehyde.

Surprisingly, the inventors of the present disclosure have found that the use of bis-maleic anhydrides as a cross-linking agent in the preparation/fixation of a cell or tissue sample is of tremendous advantage and can and will lead to significant improvements regarding at least one or even several of the problems in the known art.

SUMMARY OF THE DISCLOSURE

Some embodiments include methods for fixation of a sample, comprising: the step of incubating a sample with a bis-maleic anhydride according to Formula I, Formula I wherein R1 and R2 independently are selected from the group consisting of hydrogen, methyl, ethyl, propyl, isopropyl and butyl, wherein X is a linker with between 1 and 30 atoms in length, wherein the sample includes at least one tissue and/or at least one cell and wherein the incubation step results in a fixed sample. In some embodiments R1 is hydrogen or methyl and R2 is hydrogen or methyl. In some embodiments R1 and R2 are the same. In some embodiments the linker X is 1 to 20 atoms in length. And in some embodiments the linker X includes at least one carbon atom and optionally one or more heteroatom(s) selected from O, N and S. In some embodiments the linker X includes at least one atom selected from the group consisting of C, O, N or S. In some embodiments the linker X includes at least one of the following groups: an alkyl group, an ester, an ether, and amide or a thio.

In some methods the incubation which includes contacting a tissue or cell sample with a least one compound according to Formula I lasts for 1 hour to 72 hours. Some embodiments include the step of embedding the fixed sample in paraffin. Still other embodiments include the further steps of: a) embedding the fixed sample in paraffin; b) de-paraffinizing said sample; c) removing the bis-maleic amide cross-link; and e) detecting an epitope of interest immunologically.

In some embodiments the epitope of interest in a given fixed tissue and/or cell sample is an epitope that is rendered difficult or impossible to detect when said epitope is present in a sample fixed with a formaldehyde fixative. Such epitopes may be damaged. blocked, destroyed, and/or otherwise altered so as to make it difficult if not impossible to interact with a probe intended to bind to them in their native or near native state. These samples include: a) embedding the fixed sample of step (a) in paraffin; b) de-paraffinizing said sample; c) removing at least one bis-maleic amide cross-link in said sample; and d) detecting a nucleic acid of interest by in situ hybridization of the sample from step c.

In some embodiments the methods for fixing a tissue or cell sample using at least one compound according to Formula I further comprises the steps of: a) embedding the fixed sample in paraffin; b) de-paraffinizing said sample; c) removing at least one bis-maleic amide cross-link; and d) detecting a nucleic acid of interest by performing RT-PCR on said sample from step c.

In some embodiments the methods for fixing a tissue or cell sample using at least one compound according to Formula I further comprises the steps of: a) embedding the fixed sample in paraffin; b) de-paraffinizing said sample; c) removing at least one bis-maleic amide cross-link; and d) immunologically detecting the at least one polypeptide of interest and detecting the at least one nucleic acid of interest by performing RT-PCR or fluorescence in situ hybridization on the sample of step c.

In some embodiments the methods for fixing a tissue or cell sample using at least one compound according to Formula I further comprises the steps of: a) embedding the fixed sample in paraffin; b) de-paraffinizing said sample; c) removing the bis-maleic amide cross-link; d) isolating the nucleic acid; and e) analyzing the nucleic acid isolated in step (d) for mutations.

Some embodiments include methods for the fixation of a sample of tissue and/or cell that, comprise the steps of using a bis-maleic anhydride cross-linking agent for fixation of a cell or a tissue sample.

Some embodiments include methods for fixing a sample, comprising: manufacturing a bis-maleic anhydride cross-linking agent for use as a fixative for fixation of a cell or tissue sample.

Some embodiments include kits for the fixation of a biological sample; comprising; at least bis-maleic anhydride according to Formula I:

wherein R1 and R2 independently are selected from the group consisting of hydrogen, methyl, ethyl, propyl, isopropyl and butyl, wherein X is a linker, wherein said linker X includes at least one atom selected from the group C, O, N and S; and a physiological buffer.

The present disclosure relates to a method for fixation of a cell or a tissue sample in vitro wherein said cell or said tissue sample is incubated with a bis-maleic anhydride cross-linking agent, whereby said cell or said tissue sample is fixed.

Further disclosed are methods of preserving a cell or a tissue sample the methods comprising the steps of fixing a tissue sample with a bis-maleic anhydride cross-linking agent and of embedding said fixed sample in paraffin.

The present disclosure also discloses methods for performing immunohistochemistry on a cell or a tissue sample the methods comprising the steps of fixing a cell or tissue sample with a bis-maleic anhydride cross-linking agent, embedding said fixed sample in paraffin, de-paraffinizing said sample, removing the bis-maleic amide cross-link and immunologically detecting an epitope of interest.

Also described are methods for detecting in vitro a nucleic acid of interest by in situ hybridization on a cell or a tissue sample. The method comprising the steps of fixing a cell or tissue sample with a bis-maleic anhydride cross-linking agent, embedding said fixed sample in paraffin, de-paraffinizing said sample, removing the bis-maleic amide cross-link and detecting a nucleic acid of interest by in situ hybridization.

Further methods include methods for detecting in vitro a nucleic acid of interest by RT-PCR in a cell or a tissue sample the methods comprising the steps of fixing a cell or tissue sample with a bis-maleic anhydride cross-linking agent, embedding said fixed sample in paraffin, de-paraffinizing said sample, removing the bis-maleic amide cross-link and detecting a nucleic acid of interest by performing RT-PCR is given.

It is also shown that based on a method according to the present disclosure both a polypeptide of interest and a nucleic acid of interest can be detected in the same specimen prepared from a cell or tissue sample. The disclosure relates to a method for detecting in vitro at least one polypeptide of interest by immunohistochemistry and at least one nucleic acid of interest in one test sample comprising a cell or a tissue sample, the method comprising the steps of fixing a cell or tissue sample with a bis-maleic anhydride cross-linking agent, embedding said fixed sample in paraffin, de-paraffinizing said sample, removing the bis-maleic amide cross-link and immunologically detecting the at least one polypeptide of interest and detecting the at least one nucleic acid of interest by performing RT-PCR or fluorescence in situ hybridization.

The disclosure further relates to the use of a bis-maleic anhydride cross-linking agent for fixation of a cell or a tissue sample as well as to the use of a bis-maleic anhydride cross-linking agent in the manufacturing of a fixative for fixation of a cell or tissue sample.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

SEQ ID NO.: 1 CTCAGCGTACCCTTGTCC is a forward primer for the detection of HER2.
SEQ ID NO.: 2 TGTCAGGCAGATGCCCAGA is a reverse primer for the detection of HER2.
SEQ ID NO.: 3 TGGTGTGGGCTCCCCATATGTCTCCC is a probe for the detection of HER2.
SEQ ID NO.: 4 TGAAAACACCGCAGCATGTCAA is a forward primer for the detection of EGFR.
SEQ ID NO.: 5 CTCCTTCTGCATGGTATTCTTTCTC is a reverse primer for the detection of EGFR.
SEQ ID NO.: 6 TTTGGGCTGGCCAAACTGCTGGGTG is a probe for the detection of EGFR.

Although the sequence listing represents various embodiments of the present disclosure, the sequence listing is not to be construed as limiting the scope of the disclosure in any manner and may be modified in any manner as consistent with the instant disclosure and as set forth herein.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

In a first embodiment the present disclosure relates to a method for fixation of a cell or a tissue sample in vitro wherein said cell or said tissue sample is incubated with a bis-maleic anhydride according to Formula I, Formula I wherein R1 and R2 independently are selected from the group consisting of hydrogen, methyl, ethyl, propyl, isopropyl and butyl, wherein X is a linker with between 1 and 30 atoms in length and whereby said cell or said tissue sample is fixed.

The compound according to Formula I sometimes will simply be referred to as "bis-maleic anhydride cross-linking agent" or "bis-maleic anhydride".

It will be understood that "a method for fixation of" in the sense of the present disclosure is equivalent to "a method of treating", that "fixing" is equivalent to "cross-linking", "is fixed" could alternatively be phrased as "is cross-linked" and that "fixed" by and in a method of the present disclosure relates to "comprising a bis-maleic amide cross-link" or "comprise(s) a bis-maleic amide cross-link". For the sake of convenience and in light of the fact that the skilled artisan is fully aware of the meanings attached to terms like fixation, fixative or fixed, and for the sake of convenience, only these terms will generally be used throughout the description.

It will also be appreciated that in a scientifically correct sense it is not a cell or a tissue sample that is fixed or cross-linked but rather it is the biomolecules found in or associated with such samples that are cross-linked or fixed in a fixation method as disclosed in the present disclosure. The cross-links in these biomolecules may be intra-molecular as well as inter-molecular cross-links.

If at least two maleic anhydrides, linked to each other by a linker X (at least a bis-maleic anhydride), are reacted with at least two primary amines, at least two amide bounds are formed and the at least two primary amines are cross-linked via the at least two amide bonds and via the linker X. For the sake of convenience this type of cross-link in the following will be referred to as "bis-maleic amide cross-link".

The articles "a" and "an" are used herein to refer to one or to more than one (i.e., to at least one) of the grammatical object of the article.

The expression "one or more" or "at least one" denotes 1 to 20, preferably 1 to 15 also preferred 1, 2, 3, 4, 5, 6, 7, 8, 9, 10, or 12.

The present disclosure is based on the surprising and striking discovery that a bis-maleic anhydride can be used to gently and reversibly fix a cell or a tissue sample. Without being wanted to be bound to this theory the great advantages are believed to be due to the facts that a) a bis-maleic anhydride cross-linking agent rapidly and effectively forms bis-maleic amide cross-links, that b) the cross-linking agent bis-maleic acid can be easily removed whenever desired and/or as may also be that c) by using a linker X of an appropriate length less negative effects like distortion or destruction of epitopes are likely as compared to the relatively short cross-linker formaldehyde.

In order to demonstrate some of the advantages of the method according to the present application it will be helpful to discuss in more detail some tissue fixation procedures and methods that are used to prepare, e.g. procedures based on the use of formaldehyde as a fixative.

Formaldehyde-based fixatives, are often derived from formalin, which may comprise a solution that includes containing 37% w/w (=40% w/v) formaldehyde in water. Often times the working fixative is a ten-fold dilution of formalin (4 grams per 100 ml). Solutions of almost identical composition may be made with paraformaldehyde as the starting material. Paraformaldehyde is a solid polymer that changes into formaldehyde when heated (in slightly alkaline water) to 60° C. Though the phrase "fixed in 4% paraformaldehyde" is often used in the literature it is not fully correct because most of the formaldehyde in a diluted aqueous solution is present as methylene glycol which forms upon by the addition of one molecule of water to one molecules formaldehyde:

$$HCOH + H_2O \leftrightarrow H_2C(OH)_2$$

The concentration of free formaldehyde in most fixative solutions is very low. Nevertheless, it is free formaldehyde, rather than methylene glycol, that is involved in the chemical reactions of fixation.

The chemical reactions that account for fixation by formaldehyde occur primarily between primary amines, such as those present in polypeptides.

Formaldehyde fixation appears to proceed through a two-step process. In a first step formaldehyde is rapidly bound to a counterpart of the sample. This rapid binding formaldehyde step probably stops autolysis but it does little to actually stabilize the fine structure of the tissue, and it does not provide effective protection against disruptive effects of later treatments of the sample such as embedding the sample in paraffin.

In the first stage (hours), formaldehyde molecules combine with various parts of protein molecules, especially the side-chains of amino acid group of lysine and the nitrogen atoms present in peptide linkages:

$$Protein-NH_2 + H_2C(OH)_2 \leftrightarrow protein-NHCH_2OH + H_2O.$$

In the second step the bound hydroxymethyl groups are thought to react with other nitrogen atoms of the same or adjacent protein molecules, thereby generating a methylene cross-link or bridge. These methylene (—CH$_2$—) bridges, are stable and account for the insolubility and rigidity of protein-containing tissues that have been fixed using the formaldehyde. One possible reaction is as follows:

$$Protein-NH-CH_2OH + NH_2-protein \rightarrow protein-NH-CH_2-NH-protein + H_2O$$

In addition to reacting with proteins, formaldehyde may also combine with some basic lipids.

Without being bound by any single theory or explanation it is likely that the above discussed two chemical reaction steps required to "fully" fix samples using formaldehyde account for some of the difficulties encountered when working with formaldehyde-fixed material. Brief exposure to formaldehyde does not cause sufficient cross-linking to immobilize small proteins or other small analytes. And extending the formaldehyde fixation steps for too long can cause irreversible damage to components of the sample. This damage may be due primarily to formation of an excess of methylene bridges. It is generally accepted by many in the clinical pathologists that in order to ensure reasonable structural preservation a given specimen should remain in a formaldehyde solution at least over night or even for about 24 hours.

In an immunohistochemistry based analysis the epitopes of an antigen of interest must be accessible in order to bind to the primary antibody. An epitope is generally a small part of a larger molecule, such as an amino acid sequence of about 5 to about 10 amino acids which is part of a protein the epitope is the portion of the protein that specifically binds to the binding site of the primary antibody molecule. Most monoclonal antibodies recognize and bind to only one epitope. A polyclonal antiserum, on the other hand, may recognize and bind to several different epitopes.

Some attempts at reversing the unwanted negative side effects of formaldehyde fixation are known in the literature. Many of these reference may be categorized under headings such as 'antigen retrieval' or 'epitope retrieval'.

At least three different routes for antigen retrieval are broadly used alone or on combination: partial enzymatic digestion, heat and/or different chemicals supposed to reverse formaldehyde effects.

For partial proteolytic digestion e.g. an inexpensive grade of porcine trypsin (containing some chymotrypsin) is used. One rationale for using a proteolytic enzyme is that breaking some peptide bonds in the "fixed" sample will create holes in the matrix of cross-linked proteins, allowing for the entry of detecting agents e.g. antibody molecules. However, proteolytic enzymes invariably attack all proteins, including the antigen(s) of interest. The tight-rope walk then is to digest just long enough to allow for detection of antigens in the sample without destroying too many of all of the antigens in the sample. And as one can easily appreciate the conditions for digestion will vary from tissue to tissue and/or from antigen to antigen.

Most of the formaldehyde bound to a fixed tissue can be removed by heat induced antigen retrieval. However, heat can also cause the irreversible destruction of target analytes. Heat is e.g. known to destroy heat-labile epitopes or the activity of heat-labile enzymes.

Heat induced antigen retrieval is often combined with use of special "retrieval" or "extraction" buffers. However, success of these procedures cannot be predicted and the unpredictable outcome of such procedures is one of the great mysteries and challenges in the field of immunohistochemistry.

Many different buffers and pH-values (e.g. citrate; glycine/HCl—mainly for acidic pH-values ranging from about 2.5 to about 6 and alkaline buffer on basis of Tris in the pH-range of about 9 to 10) have been used, either alone or in combination with chemicals believed to reverse at least partially the negative effects of the methylene cross-links introduced by formaldehyde. Chemicals used either alone dissolved in water, or dissolved in buffer e.g. are EDTA, citraconic acid, lead thiocyante, aluminum chloride, or zinc sulfate.

The large variety of ingredients used in solutions for high temperature antigen retrieval indicates that more than one mechanism is probably involved. Most antigens can be retrieved at near neutral pH, but a more alkaline medium is needed for some and acidic conditions for others. In certain cases bonds to tissue-bound calcium ions may mask epitopes, necessitating removal of the metal ions by chelation. Other ingredients of retrieval solutions include heavy metal ions, which may expose epitopes by a coagulation-like action on proteins, and chaotropic substances which may modify the shapes of proteins by changing the structures of clusters of water molecules.

For analysis of nucleic acids, e.g. from formaldehyde-fixed paraffin-embedded (FFPE) tissue various methods of antigen (analyte) retrieval, often quite different to the ones required for immunological detection of an epitope of interest, are recommended and used in the art. Nonetheless, it is also accepted that formaldehyde fixation may have a negative impact on nucleic acids. For example, it is known that messenger RNA (m-RNA) in FFPE tissue is at least partially destroyed by fixation with formaldehyde rendering the detection of m-RNAs of more the 100 nucleotides in length a quite challenging task in samples fixed with formaldehyde.

Coming now to the properties and advantages of a bis-maleic anhydride cross-linking agent as shown in the present disclosure: The reaction of maleic anhydride with a primary amine can be depicted by the following reaction scheme:

It is important that on the one hand that the amide bond formed is rather stable during (long term) storage of a sample fixed on the basis of such reagent and that on the other hand the amide bonds can be easily broken and that the primary amines can be regained easily and under gentle conditions.

Amide bond formation between a primary amine group and a maleic anhydride group occurs rapidly at neutral and alkaline pH. Preferably the incubation of a cell or tissue sample with a bis-maleic anhydride according to Formula I is performed at a pH of 7.0 or above. Also preferred is that the pH is maintained below pH 12. Further preferred, the pH used for fixation is in the range of pH 7.0 to pH 11.0, including the boarders. Also preferred is that the incubation is performed at a pH of 7.5 to 10.0, the boarders inclusive. For obvious reasons a buffer that includes a primary amine should not be used.

Preferably the fixative will not only be buffered to stabilize the pH during fixation, but the buffer will also have a physiological salt concentration. It is further advantageous and preferred, if the bis-maleic anhydride cross-linking agent is provided in a buffer also comprising a water-miscible organic solvent. Preferred organic solvents in this context are ethanol, N,N'-dimethylformamide (DMF) and dimethyl sulfoxide (DMSO).

The amide bound formed by reaction of maleic anhydride with a primary amine is stable at alkaline pH. If stored, a sample fixed with a bis-maleic anhydride according to Formula I preferably is kept at neutral or an alkaline pH, with the same preferred ranges as given above for the fixation or incubation step.

A sample comprising cells in suspension or a small tissue sample of 1 μm³ or less can be fixed within short time, like, e.g. within 10 to 60 min. In clinical routine a tissue sample, however, will often be much larger than 1 μm³. For routine purposes it is therefore preferred that a cell or tissue sample is incubated for 1 to 72 hours with the bis-maleic anhydride cross-linking agent. As the artisan would say the cell or tissue sample is fixed for 1 to 72 hours. It is also preferred that in a method according to the present disclosure the incubation of the cell or tissue sample in the fixative comprising a bis-maleic anhydride according to Formula I is performed for 2 to 48 hours.

A bis-maleic anhydride cross-linking agent may e.g. be dissolved in an organic solvent at a high concentration and can be diluted to yield an appropriate working or final concentration. The final concentration of the bis-maleic anhydride cross-linking agent used in the incubation/fixation step may vary to some extent. Preferably the final concentration is between 0.1 and 20%. Further preferred the final concentration will be between 0.25 and 10% (% in weight per volume).

The amide bond formed between a primary amine group and a maleic anhydride group in a fixation method as disclosed in the present application can be readily broken under acidic buffer conditions. Accordingly, upon incubation in acidic pH-buffers the amide bond is broken, the bis-maleic amide cross-linking is removed and the bis-maleic anhydride can be washed away. At the same time the primary amine previously part of an amide bond with the cross-linking agent is regained and present again. Preferably a bis-maleic amide cross-link is removed by incubating a fixed sample, i.e. a sample fixed by use of a bis-maleic anhydride according to Formula I, under acidic pH. Preferably a bis-maleic amide cross-link is removed by incubation in a buffer with a pH from 2.0 to 6.5. Also preferred the buffer used for removing a bis-maleic amide cross-link will have a pH from 2.5 to 6.5, or from 3.0 to 6.0, wherein each of the boarders is inclusive. Removal occurs rapidly, the more rapid, the more acidic the buffer. Preferably the fixed sample is incubated for 2 min to 2 hours, also preferred from 5 min to 1 hour in order to remove a bis-maleic amide cross-link.

It has been found that the residues R1 and R2 may be selected from hydrogen, methyl, ethyl, propyl, isopropyl or butyl for use of the bis-maleic anhydride cross-linking agent in some of the methods disclosed in the present application.

In some embodiments of the invention, the residues R1 and or R2 according to Formula I are selected from hydrogen, methyl or ethyl. In some embodiments the bis-maleic anhydride used in methods according to the present disclosure is a bis-maleic anhydride according to Formula I, wherein R1 is hydrogen or methyl and R2 is hydrogen or methyl.

In general, if R1 and R2 are the same the amide bonds formed during fixation of a cell or tissue sample using this reagent can be reversed under the same conditions. This is generally advantageous, as it maximizes the number of amides that can be recovered in the same step. In some embodiments the bis-maleic anhydride for use in methods according to the instant disclosure is a bis-maleic anhydride according to Formula I, wherein R1 and R2 are the same.

As the skilled artisan will appreciate, now that it has been found that a bis-maleic anhydride can be used for fixation of a cell or tissue sample many compounds comprising at least two maleic anhydrides linked together by a linker region can be designed and used.

In some embodiments, the linker X in the bis-maleic anhydride for use in a method according to the present disclosure comprises between 1 and 30 atoms. The term length should be understood as comprising the number of atoms in given linker. For example, a linker of 30 atoms in length has a backbone that consists of 30 atoms.

The linker X can be designed in any way that is advantageous as the specific applications accordingly, no undue limitation or restriction would be appropriate. Nonetheless, some examples of such linkers are presented herein.

In some embodiments the bis-maleic anhydride according to Formula I for use in methods according to the present disclosure have a linker X with a backbone that includes carbon atoms and optionally one or more heteroatom(s) selected from O, N and S. In some embodiments the heteroatoms comprising the backbone of the linker X will be either O or N or both O and N.

The linker X may include side chains. In some embodiments the bis-maleic anhydride according to Formula I for use in methods according to the present disclosure have a linker X in which X has one or more side chains suitable for carrying one or more maleic anhydride groups. In some embodiments the bis-maleic anhydride according to Formula I for use in a method according to the present disclosure may have a linker X with one to three maleic acid groups attached to one or more side chains, resulting in a compound according to Formula I that include three to five maleic anhydride groups.

In some embodiments preferably the linker X in a compound according to Formula I for use in methods according to the present disclosure will have molecular weights of 10 kD or below. In some embodiments, the linker X will have molecular weights of 5 kD or below, of 3 kD or below, of 2 kD or below, or of 1 kD or below. In some embodiments the bis-maleic anhydride cross-linking agent for use in methods according to the present application will have molecular weights of 1 kD or below.

While it is possible to design and use maleic anhydride cross-linking agents comprising three, four, five or even more maleic anhydride groups, it is sometimes preferred to use a bis-maleic anyhydride cross-linking agent having exactly two maleic anhydride groups that are linked by the linker X.

In some applications, side chains in the linker X will have utility. In other applications, a linker X having a backbone without side chains may be preferred in some methods. A linker without side chains is a linker having only the atoms of the backbone and atoms that directly bound to the atoms of the backbone.

In some embodiments the bis-maleic anhydride according to Formula I for use in a method according to the present disclosure will have linkers X of 1 to 20 atoms in length.

In some embodiments the linker X in the bis-maleic anhydride according to Formula I for use in methods according to the present disclosure is selected from the group of linkers consisting of linkers having of 1 to 30 atoms in length with a backbone that includes carbon atoms and optionally one or more heteroatom(s) selected from O, N and S; a linker of 1 to 20 methylene ($-CH_2-$) units; a linker of between 3 and 30 atoms consisting of methylene ($-CH_2-$), ethylene ($-C_2H_4-$) and/or propylene ($-C_3H_6-$) units and oxygen, wherein the number of ether bonds with oxygen is from 1 to 8, a linker of a backbone of 5 to 30 atoms comprising methylene groups and 1 to 4 carbonyl units bound via ester or amide bond, or a linker of between 11 to 30 atoms comprising 6 to 25 methylene groups, 2 carbonyl units bound via ester or amide bond and in addition 1 to 6 oxygen atoms linked by ether bond.

In some embodiments the linker X in the bis-maleic anhydride according to Formula I for use in a method according to the present disclosure is selected from the group of linkers consisting of a linker of 1 to 30 atoms in length with a backbone consisting of carbon atoms and optionally one or more heteroatom(s) selected from 0, N and S; a linker of 1 to 6 methylene ($-CH_2-$) units; a linker of between 3 and 30 atoms consisting of methylene ($-CH_2-$), ethylene ($-C_2H_4-$) and/or propylene ($-C_3H_6-$) units and oxygen, wherein the number of ether bonds with oxygen is from 1 to 8, a linker of a backbone of 5 to 30 atoms comprising methylene groups and 1 to 4 carbonyl units bound via ester or amide bond, or a linker of between 11 to 30 atoms comprising 6 to 25 methylene groups, 2 carbonyl units bound via ester or amide bond and in addition 1 to 6 oxygen atoms linked by ether bond.

In some embodiments the bis-maleic anhydride according to Formula I for use in a method according to the present disclosure will have a linker X of 1 to 20 methylene ($-CH_2-$) units. Preferably such type of linker will have 1 to 8 methylene units and also preferred 2 to 6 methylene units.

In some embodiments the present disclosure relates to a bis-maleic anhydride according to formula I, wherein the linker X consists of five methylene units.

In some embodiments the bis-maleic anhydride according to Formula I for use in a method according to the present disclosure will have a linker X of between 3 and 30 atoms consisting of methylene ($-CH_2-$), ethylene ($-C_2H_4-$) and/or propylene ($-C_3H_6-$) units and oxygen, wherein the number of ether bonds with oxygen is from 1 to 6.

An example of such linker is given in Formula II below.

Formula II

Such linker may comprise from 4 to 8 methylene, ethylene (—$C_2H_4$—) and/or propylene (—$C_3H_6$—) units and from 1 to 8 ether bonds. Also preferred the linker will have 4 to 6 methylene units and 1 or 2 ether bonds.

In some embodiments the bis-maleic anhydride according to Formula I for use in a method according to the present disclosure will have a linker X with a backbone of 5 to 30 atoms comprising methylene groups and 1 to 4 carbonyl units bound via ester or amide bond. The linker X may be 8 to 20 atoms in length, comprising 4 to 16 methylene groups and 2 to 4 carbonyl units bound via ester or amide bonds in the backbone of the linker X. In some embodiments the linker X will comprising 4 to 12 methylene groups and 2 to 4 carbonyl units bound via either ester or amide bonds into the backbone of the linker. In another embodiment the linker X will comprise 4 to 8 methylene groups and 2 carbonyl units bound via either ester or amide bonds into the backbone of the linker. No limitations of such bis-maleic anhydrides are given in Formulas III and IV below.

Formula III

-continued

Formula IV

In some embodiments the bis-maleic anhydride according to Formula I for use in methods according to the present disclosure will have a linker X of between 11 to 30 atoms comprising 6 to 25 methylene groups, 2 carbonyl units bound via ester or amide bond into the backbone of the linker X and in addition 1 to 6 oxygen atoms linked by ether bond. Some non-limiting examples are depicted in Formulas V to VII below.

Formula V

Formula VI

Formula VII

The cell or tissue samples may comprise samples derived from an in vitro cell or tissue cultures or may represent samples available from clinics. In some embodiments the cell or tissue sample will include cells of interest as investigated in the clinical setting. In the field of oncology such cell or tissue sample may e.g. comprise circulating tumor cells or be a tissue suspected or known to contain tumor such as and/or cancer cells. In some embodiments the samples are whole blood and tissue samples, specimens obtained by either surgery or biopsy.

As the skilled artisan will appreciate, many of the methods according to the present disclosure can be practiced in vitro. The patient sample may be stored or discarded after the analysis. Generally, the sample is not transferred back into the patient's body.

Cells as those present contained in blood are usually at least partially isolated from blood plasma before fixation. These cells may be fixed either in suspension or embedded into agar. A sample of tissue, as e.g. obtained by resection or biopsy, usually is either briefly washed in a physiological buffer or directly transferred into a solution that includes an appropriate fixative agent.

As mentioned further above, formaldehyde fixation is thought to proceed through a two-step process and therefore not easy to control. The bis-maleic anhydrides as used in methods according to the present disclosure have the tremendous advantage over formaldehyde that they require that only one type of reaction occur, the formation of an amide bond. Once at least two amide bonds are formed between at least two primary amines and maleic anhydride groups, linked to each other via the linker X. Cross-linking occurs. No formation of a methylene bridge necessitating a second chemical reaction is required.

Fixation of a cell or tissue sample—despite being probably the most critical step—is in most cases only one out of several potentially critical steps in a given clinical routine.

Usually cell or tissue samples are investigated microscopically. To that end the sample has to be prepared such that it has the appropriate thickness for staining and microscopic investigation. In case of tissue samples, usually a frozen sample or a so-called paraffin block (see below) is cut with a microtome in so-called thin sections. Thin sections usually are 2 to 10 μm thick. In some instances, the sample is a tissue sample the analytic method used in the investigation of such sample is performed on a thin section of the tissue.

In clinical pathology, it is routine procedure to take measures that allow for the long term storage of a cell or tissue sample. While e.g. tissue preservation can also be obtained by low temperature storage (e.g. at about −70° C.), routine storage conditions are either storage at 4-8° C. or even storage at ambient temperature.

After fixation of a cell or tissue sample, in methods as disclosed herein above, direct use of such samples after removal of the bis-maleic anhydride cross-linking agent, for further analysis is possible and represents a preferred embodiment of the invention. The sample may be analyzed using any of the methods given below in more detail for FFPE material.

After fixation of a cell or tissue sample, using some of the methods as disclosed herein above, embedding the fixed sample in paraffin is one of several options; it is the procedure most widely used in the clinical routine. Paraffin-embedding itself represents an intermediate step between fixation and analysis.

For long term storage at e.g. ambient temperature it is standard practice that a cell or a tissue sample is dehydrated and embedded in an appropriate medium. The skilled artisan is fully aware of procedural details and those need not to be given here. It is also preferred to practice the methods disclosed in the present application with machines for automatic tissue processing, like embedding, deparaffinizing and/or staining samples.

In many clinical routine procedures, paraffin is widely used to embed and preserve a sample for later analysis by histopathology, immunohistochemistry and so on. One of the methods according to the present disclosure is compatible with a variety of routine methods for embedding a sample in paraffin. Therefore, in some embodiments, the present disclosure relates to methods of preserving a cell or a tissue sample the method comprising the steps of:

a) fixing a tissue sample with a bis-maleic anhydride cross-linking agent; and b) embedding said fixed sample of step (a) in paraffin.

By using this process, it is possible to obtain a paraffin block that can easily be cut into thin sections.

Once embedded, the cell or tissue sample may be stored for later analysis. An analysis of the stored sample may be performed within hours or days or as the case may be several years later. Before any analysis can be performed, on e.g. a section of paraffin embedded tissue, it is necessary to remove the paraffin and to rehydrate the sample of interest. Various methods for removal of paraffin are available and the skilled artisan will have no difficulty removing paraffin for a sample using an appropriate method.

As mentioned above, various types of analyses may be performed on a cell or a tissue sample. Usually morphology, enzymatic activity, immunoreactivity and/or nucleic acids is/are assessed. As will be appreciated each of these types of assessments will to a large extent depend on the degree of structural and functional preservation of the sample to be investigated.

Investigating the enzymatic properties of a sample is usually not possible if formaldehyde is used as a fixative, because of the often observed negative effects of formaldehyde on enzymatic activity. Due to the gentle fixation of some of the methods disclosed herein, it is more likely that a given sample retains at least some of its enzymatic activity. Some embodiments of the instant disclosure relates to methods for analyzing enzymatic activity in a cell or tissue sample. The methods comprising the steps of fixing the sample with a bis-maleic anhydride cross-linking agent, removing the bis-maleic amide cross-link and analyzing the sample for the enzymatic activity.

Methods of fixation with a bis-maleic cross-linking agent according to the present application can be used with great advantage in routine procedures of immunohistochemistry. Accordingly, some embodiments of the present disclosure relate to methods for performing immunohistochemistry on a cell or a tissue sample, the method comprising the steps of:
 a) fixing a cell or tissue sample with a bis-maleic anhydride cross-linking agent;
 b) embedding said fixed sample of step (a) in paraffin;
 c) de-paraffinizing said sample;
 d) removing the bis-maleic amide cross-link; and
 e) immunologically detecting an epitope of interest in the sample.

Some embodiments of the disclosure relate to methods comprising fixing a cell or tissue sample as disclosed in the present disclosure, the methods further comprising the steps of:
 a) embedding the fixed sample in paraffin;
 b) de-paraffinizing said sample;
 c) removing the bis-maleic amide cross-link; and
 d) immunologically detecting an epitope of interest in the sample.

If a cell or tissue sample is fixed with a bis-maleic cross-linking agent and the bis-maleic amide cross-link is released before analysis, the primary amine as originally present in the sample becomes available again. This represents a major advantage over other fixatives, like formaldehyde, that are known for their often detrimental and irreversible effects on many epitopes. The negative impact of compounds such as formaldehyde may be especially critical if the single epitope of interest in a given sample recognized by a monoclonal antibody is affected, damaged, blocked, or otherwise rendered incapable of binding to the primary antibody used to probe for the epitope of interest. Many potentially valuable monoclonal antibodies have gained little attention and market penetration because they do not work in standard immunohistochemistry based on formalin-fixed paraffin embedded tissue (FFPET) samples. It is quite likely that many monoclonal bodies that fail using FFPET will work on a sample fixed with a bis-maleic anhydride cross-linking agent. Some preferred embodiments of the present disclosure relates to an immunohistochemistry method essentially as described in the previous paragraph with the additional feature that the epitope of interest is an epitope that is masked or destroyed when said cell or tissue sample comprising said epitope is fixed with a formaldehyde fixative. In other words, the inventive methods are practiced using an antibody that does not work with FFPET. In some embodiments, a given antibody may work with FFPET, but it works as well or better with a bis-maleic anhydride according to the present invention.

As described above, the methods disclosed in the present application work well with polypeptides having e.g. enzymatic or antigenic properties. Surprisingly the method disclosed herein also is of advantage in the detection of a nucleic acid of interest.

In some embodiments, the nucleic acid is a deoxyribonucleic acid (DNA) as for example present in the nucleus of a eukaryotic cell. DNA in some preferred embodiments is analyzed by an in situ hybridization method. Methods for in situ hybridization (ISH) are well-known to the skilled artisan. Gene amplification can e.g. be measured with in situ hybridization methods, like fluorescence in situ hybridization techniques (FISH), chromogenic in situ hybridization techniques (CISH) or silver in situ hybridization techniques (SISH). In some embodiments, the present disclosure relates to methods for detecting in vitro a nucleic acid of interest by in situ hybridization on a cell or a tissue sample the methods comprising the steps of:
 a) fixing a cell or tissue sample with a bis-maleic anhydride cross-linking agent;
 b) embedding said fixed sample of step (a) in paraffin;
 c) de-paraffinizing said sample;
 d) removing the bis-maleic amide cross-link; and
 e) detecting a nucleic acid of interest in the sample by in situ hybridization.

Some embodiments of the disclosure relate to methods comprising fixing a cell or tissue sample as disclosed in the present disclosure the methods further comprising the steps of:
 a) embedding the fixed sample of step (a) in paraffin;
 b) de-paraffinizing said sample;
 c) removing the bis-maleic amide cross-link; and
 d) detecting a nucleic acid of interest by in situ hybridization.

Surprisingly, the fixation methods described in the present disclosure also is of advantage in the detection of m-RNA in a cell or tissue sample prepared using a bis-maleic anhydride cross-linking agent. The expression level of an m-RNA of interest may be determined by appropriate techniques, such as Northern Blot, real time polymerase chain reaction (RT-PCR) and the like. All these detection techniques are well known in the art and can be deduced from standard text books, such as Lottspeich (Bioanalytik, Spektrum Akademischer Verlag, 1998) or Sambrook and Russell (2001, Molecular Cloning: A Laboratory Manual, CSH Press, Cold Spring Harbor, N.Y., USA). In some embodiments, m-RNA is detected using the real time polymerase chain reaction (RT-PCR). Some preferred embodiments of the present disclosure relate to methods for detecting a nucleic acid of interest in vitro by RT-PCR in a cell or a tissue sample method comprising the steps of:
 a) fixing a cell or tissue sample with a bis-maleic anhydride cross-linking agent by a method as described herein above;
 b) embedding said fixed sample of step (a) in paraffin;
 c) de-paraffinizing said sample;
 d) removing the bis-maleic amide cross-link; and
 e) detecting a nucleic acid of interest in the sample by performing RT-PCR.

Some embodiments of the disclosure relate to methods comprising fixing a cell or tissue sample as disclosed in the present disclosure the methods further comprising the steps of:
 a) embedding the fixed sample in paraffin;
 b) de-paraffinizing said sample;
 c) removing the bis-maleic amide cross-link; and
 d) detecting a nucleic acid of interest in the sample by performing RT-PCR.

In still other preferred embodiments, a nucleic acid is isolated from a cell or tissue sample that had been fixed using a bis-maleic anhydride cross-linking agent and the isolated nucleic acid is further analyzed. In some embodiments, the isolated nucleic acid is used for mutation analysis. Some embodiments of the present disclosure therefore relate to methods for performing a mutation analysis in vitro on an nucleic acid sample isolated from a cell or a tissue sample, the method comprising the steps of:
 a) fixing a cell or tissue sample with a bis-maleic anhydride cross-linking agent;

b) embedding said fixed sample of step (a) in paraffin;
c) de-paraffinizing said sample;
d) removing the bis-maleic amide cross-link;
e) isolating the nucleic acid; and
f) performing mutation analysis using the nucleic acid isolated in step (e) from the sample.

In some embodiments, the disclosure relates to methods comprising fixing a cell or tissue sample as disclosed in the present disclosure the methods further comprising the steps of:
a) embedding the fixed sample in paraffin;
b) de-paraffinizing said sample;
c) removing the bis-maleic amide cross-link;
d) isolating the nucleic acid; and
e) performing mutation analysis using the nucleic acid isolated in step (d) isolated from the sample.

Determining the presence or absence of a particular mutation in a sample of nucleic acid can be performed in a variety of ways. Such methods include, but are not limited to, PCR, hybridization with allele-specific probes, enzymatic mutation detection, chemical cleavage of mismatches, mass spectrometry or DNA sequencing, including mini-sequencing and the like. In some embodiments, hybridization with allele specific probes can be conducted in two formats: (1) allele specific oligonucleotides bound to a solid phase (glass, silicon, nylon membranes) and the labeled sample in solution, as in many DNA chip applications, or (2) bound sample (often cloned DNA or PCR amplified DNA) and labeled oligonucleotides in solution (either allele specific or short so as to allow sequencing by hybridization). Preferably, the determination of the presence or absence of a mutation involves determining an appropriate nucleotide sequence comprising the site of mutation by methods such as polymerase chain reaction (PCR), DNA sequencing, oligonucleotide hybridization or mass spectrometry.

Using the methods disclosed herein one can detect a nucleic acid of interest and a polypeptide of interest in the same sample. Further preferred embodiments of the present disclosure relate to methods for detecting in vitro at least one polypeptide of interest by immunohistochemistry and at least one nucleic acid of interest in one test sample comprising a cell or a tissue sample, the methods comprising the steps of:
a) fixing a cell or tissue sample with a bis-maleic anhydride cross-linking agent;
b) embedding said fixed sample of step (a) in paraffin;
c) de-paraffinizing said sample;
d) removing the bis-maleic amide cross-link; and
e) immunologically detecting the at least one polypeptide of interest and detecting the at least one nucleic acid of interest in the sample by performing RT-PCR or fluorescence in situ hybridization.

Some embodiments of the disclosure relate to methods comprising fixing a cell or tissue sample as disclosed in the present disclosure the methods further comprising the steps of:
a) embedding the fixed sample in paraffin;
b) de-paraffinizing said sample;
c) removing the bis-maleic amide cross-link; and
d) immunologically detecting the at least one polypeptide of interest, and detecting the at least one nucleic acid of interest in the sample by performing RT-PCR or fluorescence in situ hybridization.

As discussed above and as further illustrated in the Examples given, the use of a bis-maleic anhydride cross-linking agent has great advantages in many respect over other fixatives and procedures used in the routine of an up-to-date pathology laboratory. In a very preferred embodiment the present disclosure thus relates to the use of a bis-maleic anhydride cross-linking agent for fixation of a cell or a tissue sample.

In yet a further preferred embodiment a bis-maleic anhydride cross-linking agent is used in the preparation of a ready-to-use fixative. Preferably the present disclosure thus relates to the use of a bis-maleic anhydride in the manufacturing of a fixative for fixation of a cell or tissue sample.

Preferably the bis maleic anhydride cross-linking agent used for fixation of a cell or a tissue sample or in the manufacturing of a fixative for fixation of a cell or tissue sample will be a bis-maleic cross-linking agent as defined in Formula I. Preferably the linker X of Formula I will be selected from the group of linkers disclosed as preferred when practicing the fixation method disclosed in the present disclosure. In a further embodiment a cross-linking agent will be selected from a compound as described in Formula II, III, IV, V, VI, VII, VIII and IX.

Now that the advantages of using the bis-maleic anhydride cross-linking agents disclosed herein are known, especially how easy one can reverse their fixative effects on a given sample, one can design procedures that combine these reagents with other fixatives, e.g. with fixatives that result in a more permanent fixation. Accordingly, it is possible to further improve the long term preservation of a tissue sample, and to retain the option to regain at least one relevant portion of a nucleic acid or an antigen of interest in the sample.

Other preferred embodiments of the present disclosure relate to methods of fixing a cell or a tissue sample wherein a mixture comprising a bis-maleic acid anhydride cross-linking agent and a second cross-linking agent selected from formaldehyde and/or glutardialdehyde are used. Preferably such mixture is at least one of those described hereinafter. Still other embodiments of the invention relate to fixatives comprising a bis-maleic acid anhydride cross-linking agent and a fixative selected from formaldehyde and/or glutardialdehyde. The other components of such fixative can be selected from the preferred embodiments given for a bis-maleic anhydride fixative above. Preferably the volume-based ratio of the bis-maleic anhydride cross-linking agent to either formaldehyde or glutardialdehyde or to the sum of both if a mixture is used will be from 1:10 to 10:1 (weight/weight). The final concentration of the sum of fixatives in such mixture will be as outlined above for a fixative including only a bis-maleic anhydride cross-linking agent. Preferably such fixative mixtures comprising a bis-maleic anhydride cross-linking agent and either formaldehyde or glutardialdehyde or both will have a pH in the range of from pH 8.0 to 11.0.

The following examples, sequence listing and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It is understood that modifications can be made in the procedures set forth without departing from the spirit of the disclosure.

EXAMPLES

Example 1

While the foregoing disclosure has been described in some detail for purposes of clarity and understanding, it will be appreciated by one skilled in the art, from a reading of the disclosure that various changes in form and detail can be made without departing from the true scope of the disclosure in the appended claims.

Synthesis of "bis-citraconic acid" of Formula VIII

Formula VIII

Synthesis of methyl-3-tolylcarbamoyl-acrylic acid

To a solution of 3.2 ml 3-methyl-furan-2,5-dione (citraconic anhydride) in 25 ml ethyl ether a solution of 3.74 g p-tolylamine in 25 ml ethyl ether was added dropwise over a period of 15 min. The yellow suspension was stirred for 1 h and filtrated. The residue was washed with ethyl ether and dried under vacuum. Yield: 7.22 g, 94%

Synthesis of 3-methyl-1-p-tolyl-pyrrole-2,5-dione 7.22 g of methyl-3-tolylcarbamoyl-acrylic acid were suspended in 60 ml acetic anhydride. The suspension was heated under reflux for 3 h. After cooling to room temperature the solvent was removed under vacuum. The residue was recrystallized from ethanol. Yield: 4.32 g, 65%

Synthesis of 3-(5-(4-methyl-2,5-dione-1-p-tolyl-2,5-dihydro-1H-pyrrol-3-yl)-pentyl-)-4-methyl-1-p-tolyl-pyrrole-2,5-dione 12 g 3-methyl-1-p-tolyl-pyrrole-2,5-dione and 15.6 g triphenyl-phosphane are dissolved in 155 ml acetic acid and 2.15 ml pentanedial are added. The reaction mixture was refluxed for 20 h. The acedic acid was removed by distillation and the residue heated up to 150-160° C. for 6 h.

The crude product was purified by column chromatography on silica gel, petrolether:acedic acid ethyl ester 7:3. The product was further purified by digestion in methanol, filtrated and dried. Yield: 2 g, 35%

Synthesis of 3-(5-(4-methyl-2,5-dioxo-2,5-dihydro-furan-3-yl)-pentyl)-4-methyl-furan-2,5-dione ("bis-citraconic acid")

1.07 g of 3-(5-(4-methyl-2,5-dione-1-p-tolyl-2,5-dihydro-1H-pyrrol-3-yl)-pentyl-)-4-methyl-1-p-tolyl-pyrrole-2,5-dione were dissolved in 30 ml of a 1:1 mixture of tetrahydrofuran and methanol. After the addition of 3.48 g potassium hydroxide dissolved in water the mixture was heated under reflux for 3 h. The solvent was removed by distillation and the residue was purified by column chromatography on silica gel, petrolether:acedic acid ethyl ester 7:3. The product was dried under vacuum. Yield: 402 mg, 60%

Example 2

Synthesis of 3-(5-(4-methyl-2,5-dioxo-2,5-dihydro-furan-3-yl)-3-oxa-pentyl)-4-methyl-furan-2,5-dione (Formula IX)

Formula IX

The cross-linking agent 3-(5-(4-methyl-2,5-dioxo-2,5-dihydro-furan-3-yl)-3-oxa-pentyl)-4-methyl-furan-2,5-dione (Formula IX) is synthesized analogous to the procedure described in Example 1 using 3-oxa-1,5-pentanedial instead of 1,5-pentanedial. The starting material 3-oxa-1,5-pentanedial is described by Bowers, S. et al., Bioorganic & Medicinal Chemistry Letters 19 (2009) 6952-6956.

Example 3

Staining with an Antibody to IGF-1R

H322M xenograft tumor bearing SCID beige mice were sacrificed. The tumors were removed and were cut into 3 pieces of approximately the same size. The tissue samples were subsequently transferred into the respective fixation solutions. For fixation with bis-citraconic acid this substance was resolved in DMSO to a final concentration of 80% by repeated pipetting at room temperature. After complete dissolution this solution was either used directly or diluted 1:1 in DMSO and further diluted in 1× PBS pH 7.4, resulting in PBS with a final concentration of 10% DMSO and 8% or 4% of bis-citraconic acid, respectively. To test the impact of different concentrations of bis-citraconic acid on fixation efficacy, solutions containing 4% or 8% bis-citraconic acid (w/v) were prepared. For preparation of the formaldehyde fixative, formalin (40% (w/v) paraformaldehyde in $H_2O$) was diluted 1:10 in 1× PBS pH 7.4.

All tumor samples were fixed over night for 12 h at room temperature. The next day the tissue samples were washed with $H_2O$ for 1 h. Afterwards the fixed tumor tissues were embedded in paraffin.

Figure 1:
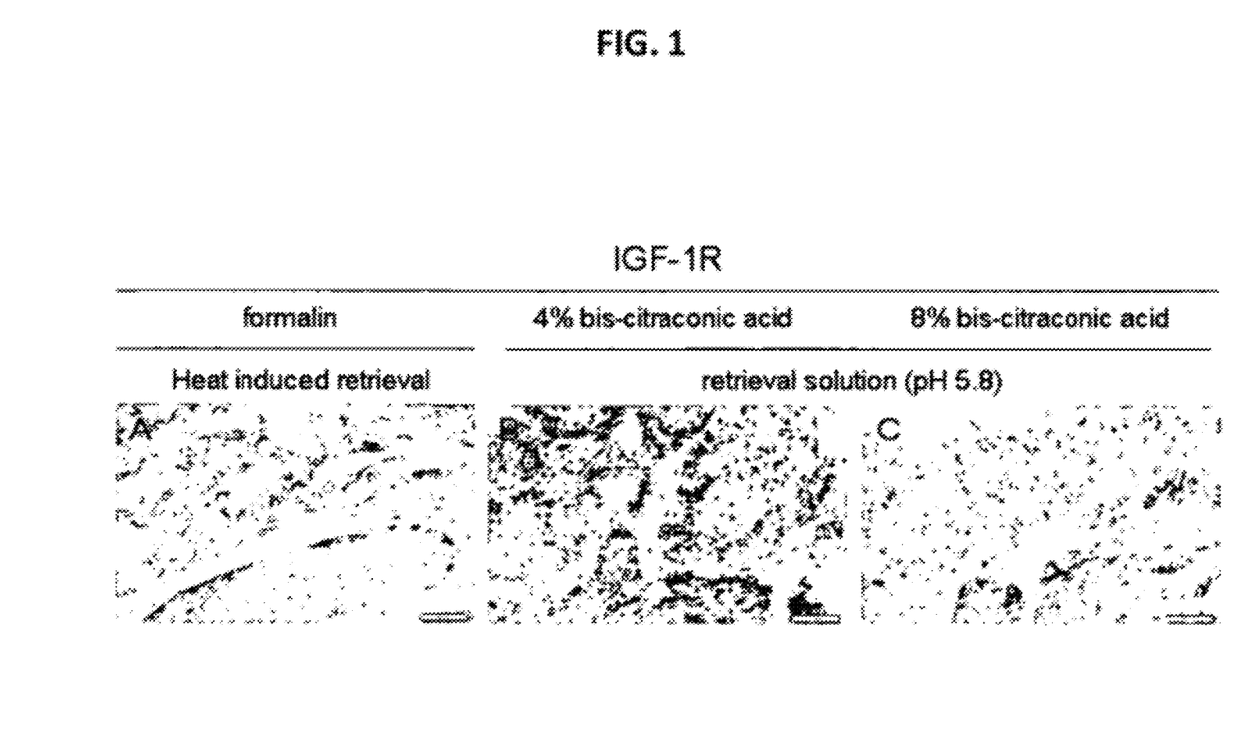
FIG. 1 shows stained 4 μm thin sections obtained from H322M xenograft tumor bearing SCID beige mice stained with monoclonal antibody 5G11 that specifically binds to IGF-1R. Tissue fixation had been performed with different fixatives using 4% formaldehyde ("formalin"), 4% or 8% bis-citraconic acid, respectively. Immunohistochemical localization of IGF-1R after heat-induced antigen retrieval for formaldehyde-fixed tissue and removal of bis-citraconic acid from tissue fixed with bis-citraconic acid by use of an acidic buffer, respectively, demonstrated comparable staining intensity or quality between the fixatives formalin (FIG. 1; A) or bis-citraconic acid used at 4% (FIG. 1: B) and 8% (FIG. 1: C), respectively.

Sections of the paraffin embedded tissue samples fixed with different fixatives (4% formalin, 4% or 8% bis-citraconic acid) were cut at 4 μm using a conventional rotation microtome. For immunohistochemical localization of IGF-1R the cut tissue sections were mounted on glass slides. Deparaffinization of the tissue samples was performed on the Ventana Benchmark XT automated IHC stainer (Ventana, Tucson). For localization of IGF-1R with the <IGF-1R>5G11 monoclonal antibody (Ventana, Tucson) in FFPE tissue by immunohistochemistry, a heat induced antigen retrieval has to be performed prior to staining of the formalin fixed sample. Heat induced antigen retrieval for immunohistochemical detection of IGF-1R was performed by incubating the tissue sections on the Ventana Benchmark XT for 1 h at 95° C. in buffer CC1 (Ventana, Tucson). Antigen retrieval in thin sections previously fixed with bis-citraconic acid and after paraffin can be performed by a simple incubation of the tissue sections in a buffer with an acidic pH. Thin sections were incubated in buffer of pH 5.8 for 2 h. After antigen retrieval, all slides were placed on the Ventana Benchmark and were stained for IGF-1R with a primary antibody incubation time of 16 min. The bound primary antibody was detected using Ventana iview DAB detection kit. Examination of the stained sections revealed that fixation of tissues with bis-citraconic acid conserved the morphology of the tissue (FIGS. 1B and C). Furthermore, the bis-citraconic acid could be retrieved by a simple incubation in an acidic buffer solution. Immunohistochemical localization of IGF-1R did not reveal great differences in staining intensity or morphological quality between formalin (FIG. 1; A) or bis-citraconic acid fixed tissues (FIG. 1; B and C).

The results obtained in this Example demonstrate that fixation with bis-citraconic acid enables conservation as well as easy and gentle retrieval of epitopes that in formalin-fixed tissues only become accessible after tissue treatment with a method known as heat-induced antigen retrieval.

Example 4

Staining with an Antibody to EGFR

Figure 2:
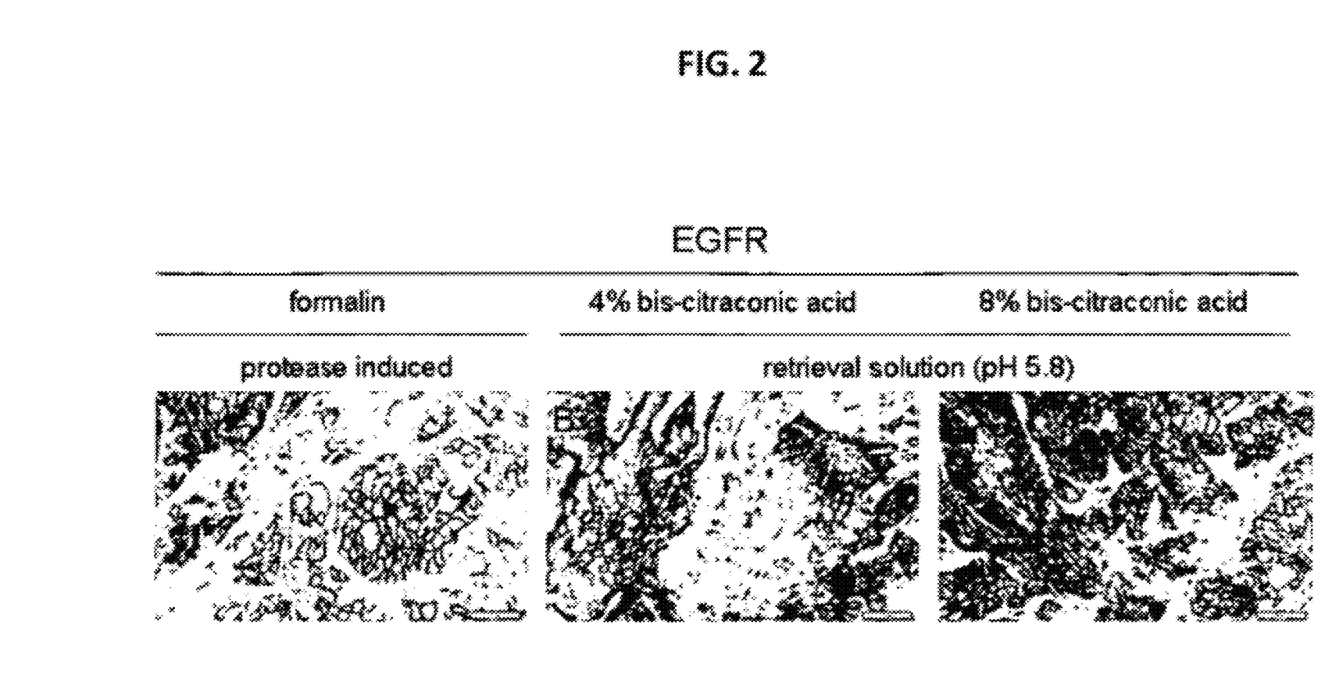
FIG. 2 shows stained 4 μm thin sections obtained from H322M xenograft tumor bearing SCID beige mice stained with monoclonal antibody 3C6 that specifically binds to EGFR. Tissue fixation had been performed with different fixatives using 4% formaldehyde ("formalin"), 4% or 8% bis-citraconic acid, respectively. Immunohistochemical localization of EGFR after protease-assisted antigen retrieval for formaldehyde-fixed tissue and removal of bis-citraconic acid from tissue fixed with bis-citraconic acid by use of an acidic buffer, respectively, demonstrated comparable staining intensity or quality between the fixatives formalin (FIG. 2: A) or bis-citraconic acid used at 4% (FIG. 2: B) and 8% (FIG. 2: C), respectively.

By a procedure similar to Example 2, formalin or bis-citraconic acid fixed tissues were prepared for staining for EGFR using the antibody 3C6 (<EGFR> mAB 3C6; Ventana, Tucson). This antibody is known to depent on a protease pretreatment of FFPE-derived tissue sections in order to regain access to its epitope in such FFPE-sample. As shown in FIG. 2, no differences in immunohistochemical localization of EGFR between formalin fixation and protease-assisted epitope retrieval or bis-citraconic acid fixation and retrieval by incubation in an acidic buffer were found.

The results obtained in this Example demonstrate that fixation with bis-citraconic acid enables conservation as well as easy and gentle retrieval of epitopes that in formalin-fixed tissues only become accessible after tissue treatment with a protease.

As demonstrated in Examples 2 and 3, collectively, bis-citraconic acid fixation and retrieval is the method for the detection of different epitopes which so far in formalin-fixed tissue have to be retrieved by one or more different retrieval methods (heat or protease induced). Bis-citraconic acid, as a prototype for other bis-maleic anhydrides, works without harsh retrieval methods for different antibodies otherwise requiring quite different methods of retrieval. Whereas heat-induced or protease-assisted retrieval is not easy to standardize and reproduce, it will be possible to obtain a more reproducible accessibility/reactivity of antigens/epitopes by use of a gentle and easy to remove fixative based on a bis-maleic anhydride cross-linking agent as shown above.

Example 5

DNA Isolation and QPCR for Gene Amplification Analysis

Figure 3:
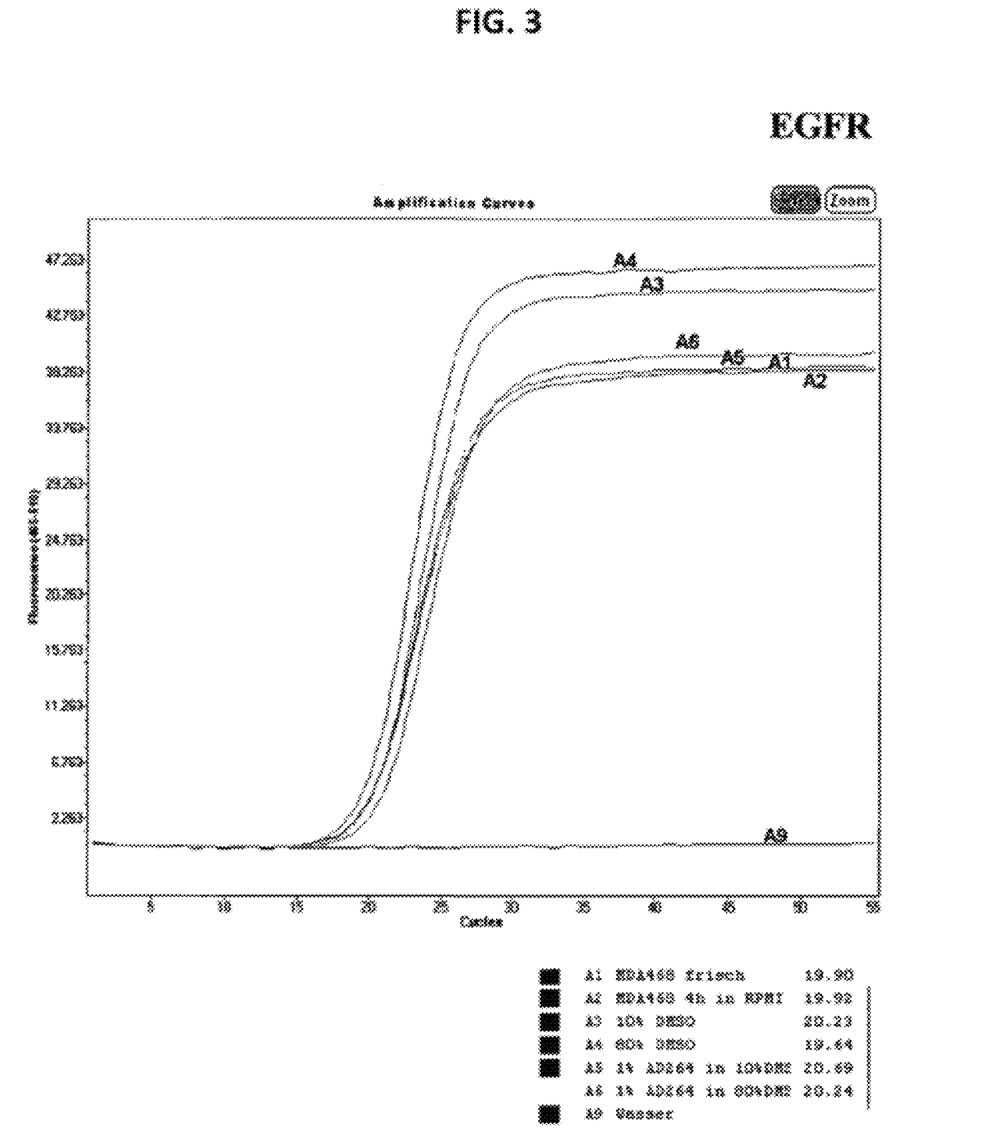
FIG. 3 shows the PCR-amplification of the EGFR-gene using mRNA isolated from MDA468 cells that had been subjected to different pre-treatment/fixation protocols. Shown are EGFR-mRNA amplifications from MDA-MB468 cells (fresh and stored for 4 hours in RPMI both not fixed, fresh MDA-MB468 cells treated/fixed in 10% DMSO, 80% DMSO, 10% DMSO with 1% bis-citraconic acid, 80% DMSO with 1% bis-citraconic acid and water "Wasser" as negative control, respectively). As obvious from the amplification curves and the inserted table, mRNA from all samples is amplified in a rather similar manner.
Figure 4:
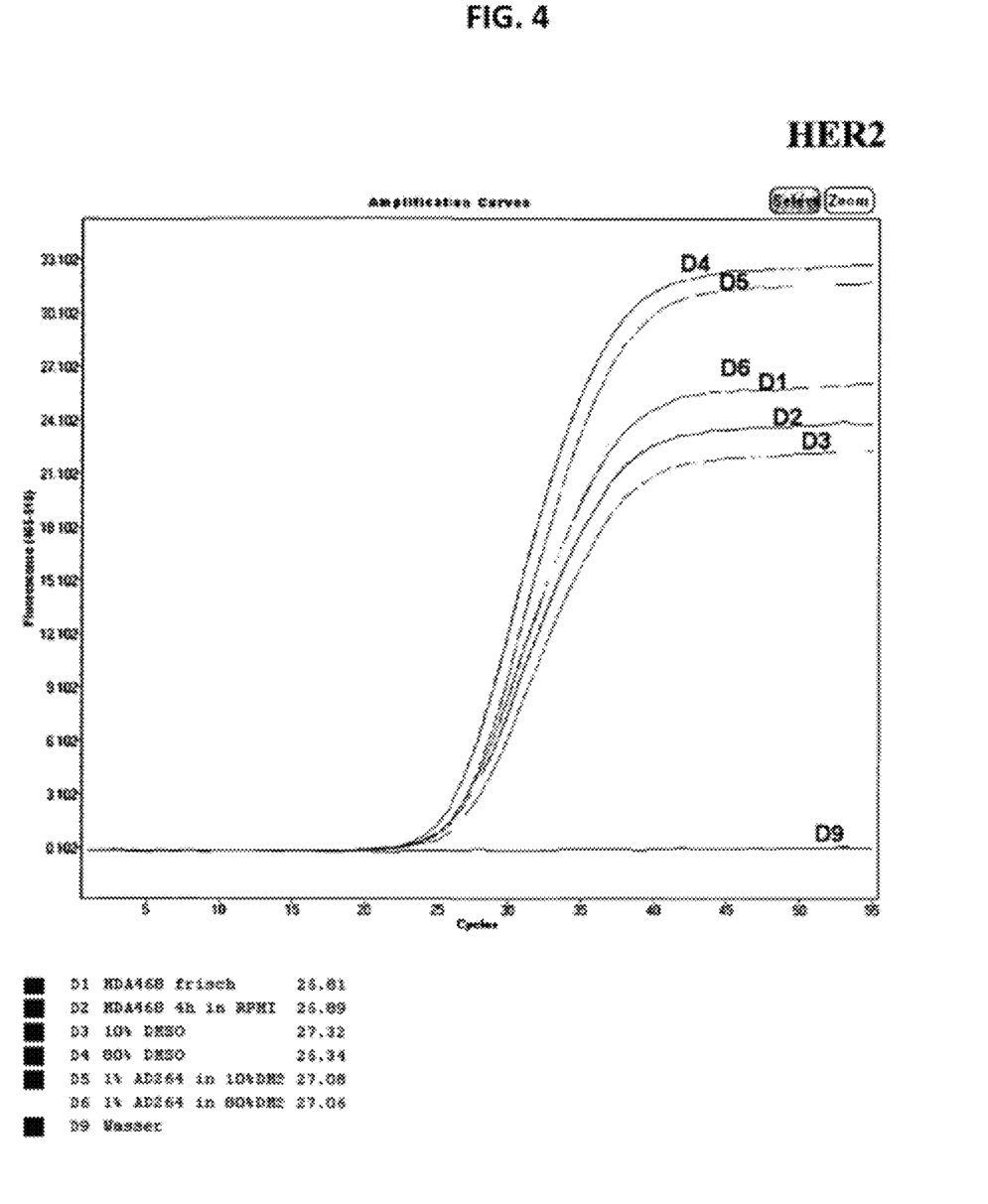
FIG. 4 shows the PCR-amplification of the HER2-gene using mRNA isolated from MDA468 cells that had been subjected to different pre-treatment/fixation protocols. Shown are HER2-mRNA amplifications from MDA-MB468 cells (fresh and stored for 4 hours in RPM both not fixed, fresh MDA-MB468 cells treated/fixed in 10% DMSO, 80% DMSO, 10% DMSO with 1% bis-citraconic acid, 80% DMSO with 1% bis-cotraconic acid and water "Wasser" as negative control, respectively. As obvious from the amplification curves and the inserted table, mRNA from all samples is amplified in a rather similar manner.

MDA-MB468 cells were first fixed in different fixation reagents for 10 min and then neutralized in citrate buffer (pH 4.4). The different samples given in FIG. 3 are MDA-MB468 cells (fresh and stored for 4 hours in RPM both not fixed, fresh MDA-MB468 cells treated/fixed in 10% DMSO, 80% DMSO, 10% DMSO with 1% bis-citraconic acid and 80% DMSO with 1% bis-citraconic acid, respectively.

After the different fixation procedures DNA isolation was performed using $1 \times 10^7$ MDA-MB468 cells. To isolate the DNA the High Pure Template Preparation Kit (Roche Diagnostics GmbH, Cat. No.: 11796828) was used according to the manufacturer's instructions. Isolated DNA was stored at −20° C.

Amplification status of the EGFR and HER2 was measured in MDA-MB468 cells. Therefore a quantitative PCR based on the use of hydrolysis probes (Taqman probes) was performed using gene specific primers and probes (see Table 1). The probes for the target genes were labeled with Fam at the 5'end and with BHQ-2 at the 3' end.

TABLE 1

Primer and Probes for the target genes HER2 and EGFR

|  | HER2 | EGFR |
|---|---|---|
| Forward Primer: | CTCAGCGTACCCTTGTCC SEQ ID NO: 1 | TGAAAACACCGCAGCATGTCAA SEQ ID NO: 4 |
| Reverse Primer: | TGTCAGGCAGATGCCCAGA SEQ ID NO: 2 | CTCCTTCTGCATGGTATTCTTTCTCT SEQ ID NO: 5 |
| Probes: | TGGTGTGGGCTCCCCATATGTCTCCC SEQ ID NO: 3 | TTTGGGCTGGCCAAACTGCTGGGTG SEQ ID NO: 6 |

For each gene an individual, verified PCR-mix was used (see Table 2).

TABLE 2

PCR-Mix Composition for the qPCR assays
PCR-Mix for EGFR, HER2:

| component | 1x (µl) |
|---|---|
| Nuclease-Free H2O | 5.5 |
| 5x RNA MasterMix | 4.0 |
| Forward Primer (500 nM) | 1.0 |
| Reverse Primer (500 nM) | 1.0 |
| TaqMan Probe (100 nM) | 0.2 |
| DMSO 100% | 0.8 |
| MgAc (25 mM) | 2.2 |
| template | 5.0 |

Each mix is composed of 5 µM forward and reverse primer and 2 µM probe. The applied Z05 polymerase was included in the COBAS Taqman RNA Reaction Mix (LUO M/N 58004938) purchased by Roche Molecular Diagnostics (Branchburg, USA) and Magnesium Acetate [25 mM] (Fluka, Cat. No.: 63049) was added in different concentrations according to the different oligo mixes. 2 µl DNA-template was used and filled up to 5 µl with nuclease free water.

Each sample was measured in triplicates. The LightCycler 480 (Roche Diagnostics GmbH) and appropriate 96-well plates and sealing foils were applied for the measurements. The following thermocycling profile was used on the cycler (Table 3).

TABLE 3

LightCycler thermocycling profile

| Program Name | Cycles | Analysis Mode |
| --- | --- | --- |
| Decontamination | 1 | Quantification |
| Amplification | 47 | Quantification |
| Cooling | 1 | None |

| Target [° C.] | Acquisition Mode | Hold | Ramp Rate [° C./s] |
| --- | --- | --- | --- |
| 50 | None | 5 min | 4.4 |
| 95 | None | 1 min | 4.4 |

TABLE 3-continued

LightCycler thermocycling profile

Amplification

| 92 | None | 15 s | 4.4 |
| --- | --- | --- | --- |
| 60 | Single | 50 s | 2.2 |

Cooling

| 40 | None | 30 s | 2.2 |
| --- | --- | --- | --- |

All publications, patents and applications are herein incorporated by reference in their entirety to the same extent as if each such reference was specifically and individually indicated to be incorporated by reference in its entirety.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A method for fixation of a sample, comprising:
incubating a sample with a bis-maleic anhydride according to Formula I, Formula I wherein R1 and R2 independently are selected from the group consisting of hydrogen, methyl, ethyl, propyl, isopropyl and butyl,
wherein X is a linker with between 1 and 30 atoms in length,
wherein the sample includes at least one tissue and/or at least one cell and wherein the incubation step results in a fixed sample.

2. The method of claim 1, wherein R1 is hydrogen or methyl and R2 is hydrogen or methyl.

3. The method of claim 1, wherein R1 and R2 are the same.

4. The method of claim 1, wherein X is 1 to 20 atoms in length.

5. The method of claim 1, wherein the backbone of the linker X includes at least one carbon atom and optionally one or more heteroatom(s) selected from O, N and S.

6. The method of claim 1, wherein the incubation step lasts for 1 to 72 hours.

7. The method of claim 1, further comprising the step of: embedding the fixed sample in paraffin.

8. The method of claim 1, the method further comprising the steps of:
a) embedding the fixed sample in paraffin, wherein the fixed sample includes at least one bis-maleic amide cross-link formed by incubating the sample with said bis-maleic anhydride;
b) de-paraffinizing said sample;
c) removing at least one bis-maleic amide cross-link from said sample of step b; and
e) detecting an epitope of interest by contacting the sample of step c with an antibody that binds to the epitope of interest.

9. The method of claim 8, wherein the epitope of interest is an epitope that is rendered difficult or impossible to detect when said epitope is present in a sample fixed with a formaldehyde fixative.

10. The method of claim 1, further comprising the steps of:
a) embedding the fixed sample in paraffin, wherein the fixed sample includes at least one nucleic acid and at least one bis-maleic amide cross-link formed by incubating the sample with said bis-maleic anhydride;
b) de-paraffinizing said sample;
c) removing at least one bis-maleic amide cross-link from the sample of step b; and
d) detecting at least one nucleic acid of interest in the sample from step c by in situ hybridization of the sample from step c.

11. The method of claim 1, further comprising the steps of:
a) embedding the fixed sample in paraffin, wherein the fixed sample includes at least one nucleic acid and at least one bis-maleic amide cross-link formed by incubating the sample with sadi bis-maleic anhydride;
b) de-paraffinizing said sample;
c) removing at least one bis-maleic amide cross-link from the sample of step b; and
d) detecting at least one nucleic acid of interest in the sample of step c by performing RT-PCR on said sample from step c.

12. The method of claim 1, further comprising the steps of:
a) embedding the fixed sample in paraffin, wherein the fixed sample includes at least one nucleic acid and/or at least one polypeptide, wherein the sample includes at least one bis-maleic amide cross-link formed by incubating the sample with said bis-maleic anhydride;
b) de-paraffinizing said sample from step a;
c) removing at least one bis-maleic amide cross-link from the sample of step b; and
d) detecting the at least one polypeptide of interest in the sample of step c by contacting the sample of step c with at least one antibody that binds to the polypeptide of interest and/or at least one nucleic acid of interest in the sample of step c by performing RT-PCR or fluorescence in situ hybridization on the sample of step c.

13. The method of claim 1, further comprising the steps of:
a) embedding the fixed sample in paraffin, wherein the fixed sample includes at least one nucleic acid and wherein the sample includes at least one bis-maleic amide cross-link formed by incubating the sample with said bis-maleic anhydride;
b) de-paraffinizing said sample from step a;
c) removing at least one bis-maleic amide cross-link formed by incubating the sample with said bis-maleic anhydride;
d) isolating at least one nucleic acid from the sample of step c; and
e) analyzing the nucleic acid isolated in step (d) for mutations.

14. A method for fixation of a sample, comprising the steps of:
contacting one of a cell and a tissue sample with a bis-maleic anhydride cross-linking agent according to Formula I:

wherein R1 and R2 are independently are selected from the group consisting of hydrogen, methyl, ethyl, propyl, isopropyl and butyl, wherein X is a linker, and wherein said linker X includes at least one atom selected from the group C, O, N and S.

* * * * *